United States Patent
Goutebroze (12)

(10) Patent No.: US 6,919,084 B2
(45) Date of Patent: Jul. 19, 2005

(54) DUCK PNEUMOVIRUS AND CORRESPONDING VACCINES

(75) Inventor: Sylvain Gabriel Goutebroze, Lyons (FR)

(73) Assignee: Merial, Lyons (FR)

( * ) Notice: Subject to any disclaimer, the term of this patent is extended or adjusted under 35 U.S.C. 154(b) by 443 days.

(21) Appl. No.: 10/155,578

(22) Filed: May 24, 2002

(65) Prior Publication Data

US 2002/0192234 A1 Dec. 19, 2002

Related U.S. Application Data

(63) Continuation of application No. PCT/FR00/03255, filed on Nov. 22, 2000.

(30) Foreign Application Priority Data

Nov. 22, 1999 (FR) .............................. 99 14952

(51) Int. Cl.[7] .............................. A61K 39/155
(52) U.S. Cl. ............... 424/211.1; 424/214.1; 424/283.1; 424/204.1; 435/236
(58) Field of Search .................. 424/211.1, 214.1, 424/283.1, 9.2, 93.1; 435/236

(56) References Cited

U.S. PATENT DOCUMENTS 6,605,460 B1 * 8/2003 Goyal ........................ 435/236

FOREIGN PATENT DOCUMENTS

| EP | 0 263 048 | 4/1988 |
|---|---|---|
| EP | 0 292 210 | 11/1988 |

OTHER PUBLICATIONS

West et al., Vaccine, 1999, 18(9–10):907–919.*
Ali and Reynolds, Avian Diseases, 1999, 43:600–603.*
Gulari et al., Avian Diseases, 2001, 45:593–597.*
Cook J., The Veterinary Journal (Sep. 1, 2000) vol. 160, pp. 118–125.*

* cited by examiner

*Primary Examiner*—Laurie Scheiner
(74) *Attorney, Agent, or Firm*—Frommer Lawrence & Haug; Thomas J. Kowalski; Mark Russell

(57) ABSTRACT

An immunogenic preparation or vaccine against avian *pneumovirosis*, comprising an antigen of the avian *pneumovirus* strain C990427, in a vehicle or excipient which is acceptable from the veterinary point of view and, optionally, an adjuvant.

48 Claims, No Drawings

DUCK PNEUMOVIRUS AND CORRESPONDING VACCINES

This is a continuation of copending international application PCT/FR00/03255 having an international filing date of 22 Nov. 2000, and designating the U.S. and claiming priority from French Application No. 99/14952 filed 26 Nov. 1999.

The present invention relates to a novel strain of *pneumovirus*, to live attenuated vaccines, to inactivated vaccines, to methods for vaccinating birds, and in particular ducks, against a *pneumovirus*, and to methods for diagnosing infection with a *pneumovirus*.

Infection of chickens and turkeys with avian *pneumoviruses* (or APVs) is known. In these species, *pneumoviruses* cause serious respiratory syndromes affecting the upper respiratory tract, loss of weight, or even death of these animals. This *pneumovirosis* is also named turkey rhinotracheitis (TRT) and swollen head syndrome (SHS) in chicken, the latter also being characterized by the appearance of subcutaneous edemas on the head of the animal. Avian *pneumoviruses* can also cause drops in egg production in layers. The economic consequences of these diseases are considerable.

It is the same virus, named turkey rhinotracheitis virus (or TRTV), which causes these two diseases.

The *Pneumovirus* genus belongs to the family Paramyxoviridae, this family also comprising the genera *Paramyxovirus, Morbillivirus* and *Rubulavirus. Pneumoviruses* are nonsegmented single-stranded RNA viruses of negative polarity. They are enveloped and their capsid is helical. Unlike other Paramyxoviridae (in particular the Newcastle disease virus or NDV), Pneumoviruses possess neither hemagglutinin nor neuraminidase (Alexander D. J., Vet. Microbiol., 1990, 23, 103–114).

Avian *pneumovirus* es have been isolated from chicken or turkeys in France, Great Britain, Italy, Spain, Hungary, Germany, the Netherlands, Greece, Brazil, Mexico, Morocco, South Africa, Taiwan and Israel. A virus antigenically and genetically different from previously known viruses was also isolated in turkeys in the United States at the beginning of 1997. This virus is often named Colorado virus (Seal B. S., Virus Research, 1998, 58, 45–52; Ali et al., Avian Disease, 1999, 43, 600–603).

The various isolates of these avian *pneumoviruses* show a genetic and antigenic diversity which may allow the strains to be classified in at least two subgroups named A and B (Juhasz et al., J. Gen. Virol., 1994, 75, 2873–2880). That article cites some avian *pneumovirus* strains, in particular the strains APV 2119 (of subgroup B, originating from Italy), 657/4 (subgroup B, originating from Hungary), 872S (of subgroup B, originating from Spain) and CVL 14/1 (of subgroup A, originating from the United Kingdom).

The Colorado APV strain belongs to neither subgroup A nor subgroup B (Seal B. S., Virus Research, 1998, 58, 45–52).

Vaccination against avian *pneumoviruses* has allowed prevention of disease in turkeys and chickens. Live and inactivated vaccines are available. Vaccine strains may be from subgroup A or from subgroup B and have been isolated from turkeys or chickens. Live vaccines are attenuated on cell cultures. Live vaccines are generally used in the young in meat birds and reproducers. Inactivated vaccines are adjuvented and are indicated in booster vaccination in reproducer birds or in egg layers.

To date, only chickens and turkeys have been described as natural hosts for avian *pneumoviruses*. Experimental infection experiments with an avian *pneumovirus* of turkey origin (strain CVL 14/1, from subgroup A, described in Wyeth et al., Vet. Rec., 1986, 119, 139) have shown sensitivity to the disease and an antibody response in turkeys, chickens and pheasants. Chickens and turkeys show symptoms of upper respiratory tract infections (nasal drip, sneezing, etc.) and pheasants show symptoms of slight conjunctivitis.

In these experiments, the pigeon, the goose and the mallard duck (*Anas platyrhynchos*) appeared to be refractory to the turkey *pneumovirus* (Cough et al., Vet. Rec. 1988, 123, 58–59).

The applicant has revealed a novel avian *pneumovirus* for which the preferred host is duck.

This virus was isolated in France from organ samples originating from a flock of female reproducer mallard ducks of the Peking type (*Anas platyrhynchos*). The animals of this flock exhibited symptoms of egg drop and of mortality.

Ground material from organs was inoculated onto cultures of specific pathogen Free chick embryo cells (CECs). At the 10th passage on CECs, a *pneumovirus* was identified by immunofluorescence with a serum directed against APV strain Colorado. The immunofluorescence tests carried out with sera specific for other duck or chicken viruses remained negative (duck parvovirus, duck plague virus, duck reovirus, avian group I adenovirus, infectious bronchitis virus, Newcastle disease virus, egg drop syndrome-76 adenovirus, avian influenza virus, *paramyxovirus* type 3, infectious bursal disease virus, avian encephalomyelitis virus). An immunofluorescence test carried out with antisera specific for various avian *pneumovirus* strains of subgroup A and of subgroup B also proved to be negative. Moreover, the virus isolated by the applicant is not a hemagglutinating virus.

A *paramyxovirus* has been visualized by electron microscopy in cultures of CECs and of Vero cells infected with the virus.

These elements indicate that a novel avian *pneumovirus* which infects ducks has been isolated. This virus is antigenically different from the other turkey and chicken avian *pneumoviruses* of subgroups A and B previously known, and is distinguished from the APV strain Colorado by its host specificity.

The virus was isolated and cultured on a CEC culture, and was then adapted on a Vero cell culture. Passaging on Vero cell cultures may be used to attenuate the virus.

A subject of the present invention is a culture of this novel virus (name C990427) as deposited, on Nov. 25, 1999, with the Collection Nationale de Cultures de Microorganismes (or CNCM) [National Collection of Microorganism Cultures] of the Pasteur Institute, Paris, France, under the accession number I-2353.

A subject of the present invention is also the immunogenic preparations and the vaccines against avian *pneumovirosis*, comprising at least one antigen or immunogen of the APV strain C990427 in a vehicle or excipient which is acceptable from a veterinary point of view and, optionally, in the presence of an adjuvant.

The notion of immunogenic preparation herein covers any preparation capable, once administered to birds, of inducing an immune response directed against the avian pathogen under consideration. The term "vaccine" is intended to mean a preparation capable of inducing effective protection. The vaccines according to the invention make it possible to prevent and/or treat the infection.

Like the other avian *pneumoviruses* already known, this virus may be used to immunize or vaccinate birds, in particular gallinaceans, e.g. turkeys, hens and chickens, and more particularly ducks, especially mallard ducks (*Anas platyrhynchos*) and Muscovy ducks (*Cairina moschata*), against infection caused by avian *pneumoviruses*, and in particular against infection caused by duck *pneumoviruses*.

According to a first mode, a subject of the invention is a live attenuated immunogenic preparation or a live attenuated vaccine.

The novel virus may be attenuated by the usual methods known to those skilled in the art, in particular by 10 to 150 passages on primary cell culture, for example on CEC culture, or on cell lines, for example on Vero cells, or on embryonated eggs. The number of passages is multiplied until there is a lack of significant symptoms in animals.

To produce the vaccinal virus, the attenuated virus may then be multiplied on primary cells, for example CECs, or cells from a line, for example on Vero cells, or on embryonated eggs. The immunogenic preparation or the vaccine incorporating a suitable amount of virus multiplied in this way may be frozen or lyophilized with a stabilizer, in particular SPGA (EP-B1-0008255). Each vaccinal dose may contain from $10^2$ to $10^6$ 50% cell culture infectious doses (CCID50) per dose, and preferably from $10^2$ to $10^4$.

The attenuated immunogenic preparation or the attenuated vaccine according to the invention may also be mixed with other viral or bacteria valences so as to constitute multivalent immunogenic preparations or multivalent vaccines. The viral or bacterial valences are selected from avian pathogens characteristic of the avian species to be vaccinated. They are in particular selected from the group comprising Newcastle disease virus (NDV), infectious bronchitis virus (IBV), infectious bursal disease virus (IBDV), duck parvovirus and the other avian *pneumoviruses*, including TRTV. These other valences may in particular be conventional attenuated valences or recombined valences.

The attenuated immunogenic preparations and attenuated vaccines may be administered to birds individually by inoculation either in ovo, in particular between approximately 4 and 1 day(s) before hatching, and preferably 3 days before hatching, or via eyedrops, by dipping the beak, or by intramuscular or subcutaneous injection.

The attenuated immunogenic preparations and attenuated vaccines may be administered collectively via drinking water or nebulization.

The immunogenic preparation or vaccine may be administered after having been taken up in an adjuvented diluent, for example a diluent adjuvanted with an aqueous adjuvant such as aluminum hydroxide.

According to a second mode, a subject of the invention is an inactivated immunogenic preparation or an inactivated vaccine.

The virus may be multiplied on primary cells, for example CECs, or cells from a line, for example from Vero cells, or on embryonated eggs. Before or after inactivation, the virus thus produced may be clarified, in particular by filtration or by centrifugation, and/or may be concentrated, in particular by ultrafiltration or precipitation, and/or may be purified, in particular by selected precipitation or by chromatography. The inactivation may be carried out by the usual methods known to those skilled in the art, in particular by chemical treatment (e.g. formaldehyde, β-propiolactone, ethyleneimine, binary ethyleneimine (BET)) and/or heat treatment. The inactivated virus may then be mixed with an adjuvant, preferably an aqueous adjuvant, for example based on aluminum hydroxide, or may be formulated in the form of an emulsion, in particular a water-in-oil emulsion, composed of mineral oil or metabolizable oil and one or more nonionic surfactants. By way of example, the water-in-oil emulsion comprises polysorbate 80 (e.g. Tween® 80) in the aqueous phase, and mineral oil (e.g. Drakeol® 6VR) and sorbitan monooleate (e.g. Span® 80) in the oily phase (Stone et al., Avian Dis., 1978, 22, 666–674).

Each vaccinal dose may contain the equivalent of $10^3$ to $10^8$ CCID50 per dose, and preferably from $10^5$ to $10^7$, before inactivation. The amount of antigen per dose may also be determined by other methods using antigen/anti-body reactions, for example by the ELISA method.

The inactivated antigen may also be mixed with other viral or bacterial valences so as to constitute multivalent immunogenic preparations or multivalent vaccines. The viral or bacterial valences are selected from the avian pathogens characteristic of the avian species to be vaccinated. They are in particular selected from the group comprising Newcastle disease virus (NDV), infectious bronchitis virus (IBV), infectious bursal disease virus (IBDV), egg drop syndrome virus, duck parvovirus, *paramyxovirus* type 3 and the other avian *pneumoviruses*, including TRTV. These valences may in particular be conventional inactivated valences, recombined valences or subunit-based valences.

The inactivated immunogenic preparations and inactivated vaccines are preferably administered to birds by intramuscular or subcutaneous injection. The inactivated antigen may also consist of or comprise fractionated or subunit antigens.

A subject of the present invention is also compositions comprising the novel *pneumovirus* C990427 in live attenuated form or in inactivated form, optionally a vehicle or excipient which is acceptable from a veterinary point of view and, optionally, an adjuvant.

The contents of C990427 and the choice of adjuvants are as described above.

A subject of the present invention is also compositions comprising fractionated or subunit antigens of C990427, optionally a vehicle or excipient which is acceptable from a veterinary point of view and, optionally, an adjuvant.

A subject of the invention is also methods for immunizing or vaccinating birds, in particular ducks and gallinaceans such as hens, chickens and turkeys, against diseases due to avian *pneumoviruses*, and in particular against diseases due to duck *pneumoviruses*, methods in which an immunogenic preparation or a vaccine according to the invention is administered to the animal.

The programs for immunizing or vaccinating meat ducks may in particular comprise one or two administration(s) to animals approximately 1 to approximately 3 weeks old, with an attenuated vaccine, intramuscularly or subcutaneously, preferably with an adjuvaut, in particular an aqueous adjuvant such as aluminum hydroxide, or ocularly, preferably without adjuvant. A booster administration may be given between 2 and 4 weeks after the first administration. Preferably, when the ducks are intended for reproduction, they are also administered, around the age of 10 weeks, a new dose of live vaccine and, before the egg laying period, an inactivated vaccine adjuvented in the form of an emulsion, intramuscularly or subcutaneously.

For the other avian meat species, in particular turkeys and chickens, a live attenuated, preferably nonadjuvented, vaccine is preferably administered once or twice to young animals, in the drinking water or by nebulization. The first administration may be performed on animals approximately 14 days old. A booster administration may be given between 2 and 4 weeks after the first administration.

Preferably, when the other avian species, in particular turkeys and hens, are intended for reproduction or for egg laying, they are also administered, before the egg laying period, an inactivated vaccine which is adjuvented, preferably in the form of an emulsion, intramuscularly or subcutaneously.

Those skilled in the art have the competence necessary to define precisely the number of injections and the doses of each vaccine to be used for each vaccination protocol.

The dose volumes may in particular be between 0.1 and 0.8 ml, preferably of the order of 0.3 to 0.5 ml.

A subject of the present invention is also the use of the pneumovirus C990427, for preparing an immunogenic preparation or a vaccine intended to be administered to a bird, in particular a duck, according to the invention, said preparation or vaccine also comprising a vehicle or excipient which is acceptable from a veterinary point of view and, optionally, an adjuvant.

A subject of the present invention is also the use of an antigen or immunogen of the pneumovirus C990427, for preparing an immunogenic preparation or a vaccine intended to be administered to a bird, in particular a duck, according to the invention, said preparation or vaccine also comprising a vehicle or excipient which is acceptable from a veterinary point of view and, optionally, an adjuvant.

The invention is also directed toward such a use in the context of preparing a combined immunogenic preparation or a combined vaccine, or in the context of a combined vaccination program.

The invention also relates to the reagents used for diagnosing infection with the avian pneumovirus C990427.

This virus may be used, firstly, as a crude or purified antigen or antigen in subunit form and, secondly, in crude, purified or subunit form for immunizing animals for the purpose of producing polyclonal and monoclonal antibodies. The antigens and the antibodies can be used in the diagnostic method according to the invention and for developing diagnostic kits, in particular of the ELISA type.

The invention will now be described in greater detail using embodiments taken by way of nonlimiting examples.

EXAMPLES

Example 1

Isolation of the Virus

Organs (firstly, liver, heart, oviduct, trachea and spleen mixed together and, secondly, intestines) were removed from female reproducer mallard ducks of the Peking type (Anas platyrhynchos) exhibiting symptoms of egg drop and of mortality. The two batches of organs were ground separately in phosphate buffer (PBS) supplemented with an antibiotic (1/10 000 of gentamycin), frozen, thawed and then clarified by centrifugation. The centrifugation supernatant was diluted again in order to obtain a final dilution of the organs of approximately 1/10th (W/V) for the mixture of liver, heart, oviduct, trachea and spleen, and of approximately 1/50th (W/V) for the intestines.

The ground materials were filtered (0.22 $\mu$m).

A culture of primary SPF (specific pathogen free) chick embryo cells (CEC1) was prepared by inoculation of $3 \times 10^6$ cells per 25-cm² flask in F10-199 medium, pH 6.9 to 7.1, supplemented with 5% of fetal calf serum (FCS). The cells were incubated at 38° C. with 5% of $CO_2$.

The composition of the F10-199 medium is as follows: 60 ml of F10 (10 times concentrated), 40 ml of 199 Hanks (10 times concentrated), 40 ml of TPB, 20 ml of 5.6% bicarbonate, 1 ml of vitamins and water qs for 1 000 ml.

After 24 h of culture, the medium was discarded and a mixture of equal parts of the two ground materials was inoculated onto the CEC1 cells, in a proportion of 0.8 ml per 25-cm² flask. After 30 min of contact at 38° C., the cells were rinsed with culture medium. Culture medium supplemented with 1% of FCS was then added and the cultures were reincubated as previously (1st passage).

After three days of culture, the cells were treated with pronase, and $3 \times 10^6$ cells were reinoculated per 25-cm² flask in F10-199 medium supplemented with 3% of FCS, in order to obtain a secondary CEC culture (CEC2). The cultures were reincubated as previously for seven days (2nd passage) and were then frozen and thawed and the suspension thus obtained was clarified by centrifugation.

1 ml of the supernatant was inoculated onto a new layer of CEC1 and the culture was continued as previously (3rd passage).

Further passages, alternately on CEC2 and on CEC1, were then carried out.

At the 4th passage, some clusters of rounded and refringent cells were observed after four days of culture. From the 5th passage, plaques of rounded and refringent cells and syncitia were observed. From the 10th passage, a generalized cytopathic effect (CPE) was observed after 3 days of culture.

Example 2

Adaptation of the Virus on Vero Cells

A culture of the virus at the 11th passage on CECs, prepared in example 1, was frozen, thawed and clarified by centrifugation.

A culture of Vero cells was prepared by inoculation of $10^6$ cells per 25 cm² flasks in modified eagle medium (MEM), pH 6.9 to 7.1, supplemented with 5% of FCS. The cells were incubated at 38° C. with 5% of $CO_2$.

The composition of the MEM medium is as follows: 200 ml of MEM Earle's salt (5 times concentrated), 0.1 ml of 1% biotin, 10 ml of 200 mM glutamine, 1.5 ml of phenol red, 10 ml of 10% glucose, 30 ml of 5.6% bicarbonate and water qs for 1 000 ml.

After 24 h of culture, the medium was discarded and the virus originating from the 11th passage on CECs was inoculated in a proportion of 1 ml of the centrifugation supernatant described above per 25-cm² flask. These cells were reincubated as previously. After 6 days of culture, clusters of rounded and refringent cells and syncitia were observed and lysis plaques began to appear on the carpet of cells.

The subsequent passages on Vero cells were carried out by freezing, thawing and clarifying the cultures, and then inoculating the supernatant into a new culture of Vero cells in a proportion of 0.5 ml of supernatant per 25-cm² flask. The cells were reincubated as previously.

Each culture was harvested when the CPE became generalized, approximately 3 to 6 days after the beginning of the culture.

The viral suspension may be stored at a temperature below or equal to −40° C. before it is subsequently used.

Example 3

Characterization of the Virus by Immunofluorescence

The virus isolated according to example 1 was identified by immunofluorescence on cell cultures. Vero cell cultures in 96-well microplates were prepared, in a proportion of 1.8×10⁴ cells in 0.2 ml of MEM medium, pH 6.9 to 7.1, supplemented with 3% of FCS, per well.

After 24 h of incubation at 38° C. with 5% of $CO_2$, the medium was discarded and the virus was inoculated in a proportion of approximately 200 CCID50 in 0.2 ml of MEM medium, pH 6.9 to 7.1, supplemented with 1% of FCS. The plates were incubated as previously for 48 to 72 h. When lysis plaques began to appear on the carpet of cells, the cultures were rinsed by washing with PBS. A solution of acetone (100 ml of pure acetone+15 ml of distilled water) was added to all the wells in order to fix the cells. The plates were placed at −20° C. for 20 minutes. The acetone was then discarded and the plates were dried. The plates thus fixed can be stored at −20° C.

Sera monospecific for avian *pneumovirus* of subgroup A, for avian *pneumovirus* of subgroup B, for avian *pneumovirus* strain Colorado, for duck parvovirus, for duck plague virus, for avian reovirus, for avian group I adenovirus, for infectious bronchitis virus, for Newcastle disease virus, for egg drop syndrome-76 virus, for avian influenza virus, for *paramyxovirus* type 3; for infectious bursal disease virus and for avian encephalomyelitis virus were diluted separately to 1/20 in physiological saline. Each serum was brought into contact, separately, with the infected Vero cells, in a proportion of 100 μl of diluted serum per well.

The plates were placed in an incubator at 38° C. for 60 minutes, then the sera were removed and the plates were rinsed 3 times with physiological saline and 3 times with demineralized water.

A commercial anti-chicken fluorescent conjugate was diluted to the concentration recommended by the supplier (RACH FITC conjugate, Nordic), and then added in a proportion of 50 μl per well containing a chicken virus. A commercial anti-duck fluorescent conjugate was diluted to the concentration recommended by the supplier (RADU FITC conjugate, Nordic) and then added in a proportion of 50 μl per well containing a duck virus.

The plates were incubated for 30 minutes at 38° C., then the conjugate was removed and the plates were rinsed 3 times with physiological saline and 3 times with demineralized water.

The plates thus obtained were observed under fluorescence microscope. Intense intracytoplasmic fluorescence was observed with the serum specific for avian *pneumovirus* strain Colorado, whereas no reaction was observed with the other sera.

Example 4

Electron Microscopy

CEC (example 1) or Vero cell (example 2) cultures were inoculated with the virus. When the CPE became visible, the carpet cells were prefixed with glutaraldehyde, underwent osmic acid fixation, and were dehydrated with ethyl alcohol.

The areas of interest exhibiting the beginnings of CPE were then embedded in epoxy resin and ultrathin sections of the samples were cut and contrasted.

The observations were made using a transmission electron microscope. Penetration of the viruses by fusion of the viral envelope with the cell membrane, intracytoplasmic accumulation of nucleoprotein compounds and budding of viral particles at the level of the cytoplasmic membrane were observed. Polymorphous mature enveloped viral particles were observed in the extracellular space. Some particles are rounded and have a diameter equal to a minimum of 130 nm. Other particles are filamentous and are greater than 1 000 nm in size. Bulges sometimes exhibiting spikes are also observed. These images are characteristics of the structure and of the morphogenesis of Paramyxoviridae.

Example 5

Production of the Virus on Vero Cells

After thawing, the virus originating from the stock described in example 2 can be cultured in roller bottles.

Vero cells were prepared in MEM medium, pH 6.9 to 7.1, supplemented with 5% of FCS. The virus was mixed with the cells with a multiplicity of infection (MOI) of 1 to 0.01, and the mixture was distributed into roller bottles in a proportion of 120×10⁶ cells per roller bottle. The bottles were incubated at 38° C. When the CPE caused by the virus was optimal (more than 50% of the carpet of cells destroyed), the viral suspension was harvested after vigorous shaking of the bottles.

The harvest may be mixed at 50% with a stabilizer, for example a buffered solution. The viral suspension may be stored at a temperature of below or equal to −40° C. before it is subsequently used.

Example 6

Titering the Virus on Vero Cells

The titering was performed in 96-well microplates in MEM medium, pH 6.9 to 7.1, supplemented with 3% of FCS. Approximately 10-fold dilutions of virus were mixed with a suspension of Vero cells in the microplates, in a proportion of 0.1 ml of virus dilution per 1.8×10⁴ cells in 0.15 ml per well. After 6 to 9 days of incubation at 38° C. with 5% of $CO_2$, the wells exhibiting a generalized CPE were counted and the titer was calculated as 50% cell culture infectious doses (CCID50) by the Kärber method.

Example 7

Preparation of a Live Vaccine

After thawing of the virus obtained in example 5, the amount of virus was adjusted to the desired titer.

An SPGA stabilizer (sucrose, phosphate, glutamate and albumin, EP-B1-0008255) was added to the viral suspension, which was distributed into bottles and lyophilized. The vaccinal virus was titered as in example 6. The titer of the vaccine was adjusted to 10², 10³ and 10⁴ CCID50 per dose.

Before it is administered, the vaccinal virus may be taken up in an adjuvented diluent containing aluminum hydroxide. The adjuvant is composed of an isotonic phosphate buffer containing 2.1 grams of aluminum hydroxide per liter. The lyophilized vaccine was taken up in the diluent such that 0.5 ml of diluent contains one dose of vaccinal virus.

Example 8

Preparation of an Inactivated Vaccine

The virus was cultured according to the method described in example 5. The viral suspension was clarified by centrifugation. The virus was inactivated with formaldehyde.

A 40% formaldehyde solution was added so as to obtain a final concentration of formaldehyde of 0.1% in the viral suspension. The mixture was maintained at 37° C. for 12 h with moderate stirring, and then cooled to 5° C.

The viral suspension obtained may be concentrated 10 to 50-fold by ultrafiltration. The inactivated viral suspension, which may or may not be concentrated, may be stored at a temperature of 5° C. before it is used.

A water-in-oil emulsion is prepared by slowly adding the aqueous phase to the oily phase, over 15 min, with moderate agitation using a turbomixer. Homogenization was carried out for 10 min at 15 to 25 m/sec, and then the emulsion thus formed was cooled to 5° C. and stored at this temperature.

The aqueous phase contains the inactivated virus and 3.2% v/v of polysorbate 80 (Tween® 80).

The oily phase contains 10% v/v of sorbitan monooleate (Span® 80) and 90% v/v of mineral oil (Drakeol® 6-VR).

The aqueous phase to oily phase ratio is 1:4.

The viral suspensions for the inactivated vaccine comprise $10^{6.2}$, $10^{7.2}$ and $10^{8.2}$ CCID50 per ml.

Example 9

Vaccination Method and Program

In young ducks, the adjuvented live vaccine prepared as described in example 7 is administered subcutaneously in a proportion of one dose of 0.5 ml in the first week of life and a booster of a dose of 0.5 ml between 2 and 4 weeks after the first administration.

In reproducer ducks, the above program is used, and then a booster with the live vaccine is given around the 10th week of age. A booster with a dose of 0.3 ml of oily inactivated vaccine (example 8) is then given before each period of egglaying.

Example 10

Method of Diagnosis

The diagnosis of infection is carried out by viral isolation according to the method as described in example 1 or by serology using a seroneutralization method.

The seroneutralization is performed on Vero cell cultures in 96-well microplates. The sera to be tested are serially diluted four-fold in MEM medium, pH 6.9 to 7.1, supplemented with 1% of FCS, directly in the microtitration plates. One well per serum and per dilution is used, at a volume of 0.1 ml of diluted serum per well. The virus, used at a concentration of 200 CCID50 in 0.025 ml, is added to each well. A contact time of 30 minutes at 38° C. is used. The VERO cells are added to each well in a proportion of $1.8 \times 10^4$ cells in 0.15 ml of MEM medium, pH 6.9 to 7.1, supplemented with 1% of FCS. A negative serum, a control positive serum and also cell controls are set up for each reaction. Reading is carried out after 9 days of incubation at 38° C. with 5% of $CO_2$, under plastic film. The approximate percentage inhibition of the CPE (0%, 50%, 100%) is assessed. The last dilution which causes complete inhibition of the CPE expresses the 100% titer of the serum tested. The last dilution which causes 50% inhibition of the CPE expresses the 50% titer of the serum tested.

It should be clearly understood that the invention defined by the attached claims is not limited to the particular embodiments indicated in the above description, but encompasses the variants which depart neither from the context nor the spirit of the present invention.

What is claimed is:

1. A culture of avian *pneumovirus* named C990427 and deposited with the CNCM under the accession number I-2353.

2. An immunogenic composition or vaccine against avian *pneumovirus*, comprising the avian *pneumovirus* C990427, a sample of which is deposited with the CNCM under the accession number I-2353, in a vehicle or excipient which is veterinarily acceptable and, optionally, an adjuvant.

3. The immunogenic composition or vaccine as claimed in claim 2, comprising live attenuated virus as antigen.

4. The immunogenic composition or vaccine as claimed in claim 3, comprising an aqueous adjuvent.

5. The immunogenic composition or vaccine as claimed in claim 3, comprising from $10^2$ to $10^6$ CCID50 per dose.

6. The immunogenic composition or vaccine as claimed in claim 3, further comprising at least one additional antigen of at least one avian pathogenic agent.

7. The immunogenic composition or vaccine as claimed in claim 2, comprising inactivated virus as antigen.

8. The immunogenic composition or vaccine as claimed in claim 7, comprising an aqueous adjuvant or formulated as an emulsion.

9. The immunogenic composition or vaccine as claimed in claim 8, formulated as a water-in-oil emulsion having an aqueous phase and an oily phase and containing polysorbate 80 in the aqueous phase, and mineral oil and sorbitan monooleate in the oily phase.

10. The immunogenic composition or vaccine as claimed in claim 7, comprising from $10^3$ to $10^8$ CCID50 per dose before inactivation.

11. The immunogenic composition or vaccine as claimed in claim 7, further comprising at least one additional antigen of at least one avian pathogenic agent.

12. A method for immunizing or vaccinating a bird against avian *pneumovirus* comprising administering to the bird the immunogenic composition or a vaccine as claimed in claim 2.

13. The method as claimed in claim 12, comprising administering intramuscularly, subcutaneously or ocularly the immunogenic composition or vaccine once or twice to the bird at approximately 1 to 3 weeks of age, and, between 2 and 4 weeks after the administering, re-administering the immunogenic composition or vaccine as a booster.

14. The method as claimed in claim 13, wherein the administering is intramuscularly or subcutaneously and the immunogenic composition or vaccine comprises an aqueous adjuvant.

15. The method as claimed in claim 13, wherein the administering is ocularly.

16. The method as claimed in claim 12, wherein the bird is a duck, and the method comprises admimistering the immunogenic composition or vaccine intramuscularly or subcutaneously or ocularly once or twice to the duck at approximately 1 to 3 weeks of age, optionally between 2 and 4 weeks after the administering, re-administering the immunogenic composition or vaccine as a booster, and at 10 weeks of age before egglaying further administering the immunogenic composition or vaccine intramuscularly or subcutaneously.

17. The method as claimed in claim 2, wherein the adjuvented and inactivated immunogenic composition or vaccine is an emulsion.

18. The method as claimed in claim 2, wherein the attenuated vaccine is administered intramuscularly or subcutaneoulsy and is adjuvented with an aqueous adjuvant.

19. A method for immunizing or vaccinating a turkey or chicken against *pneumovirus* comprising administering the immunogenic composition or vaccine as claimed in claim 3, once or twice in drinking water or by nebulization.

20. The method as claimed in claim 19, wherein the method comprises administering the immunogenic composition or vaccine to the turkey or chicken at approximately 14 days of age and between 2 and 4 weeks after the administering, re-administering the immunogenic composition or vaccine as a booster.

21. A method for immunizing or vaccinating a turkey or chicken comprising administering to the turkey or chicken a first immunogenic composition or vaccine comprising avian *pneumovirus* C990427, a sample of which is deposited with the CNCM under the accession number I-2353, in a vehicle or excipient which is veterinarily acceptable, and optionally, an adjuvant, once or twice to the turkey or chicken, in drinking water or by nebulization, and before egglaying, administering to the turkey or chicken a second immunogenic composition or vaccine comprising avian *pneumovirus* C990427, a sample of which is deposited with the CNCM under the accession number I-2353, in a vehicle or excipient which is veterinarily acceptable, and optionally, an adjuvant, intramuscularly or subcutaneously, wherein the first immunogenic composition or vaccine comprises live virus as antigen, and the second immunogenic composition or virus comprises inactivated virus as antigen.

22. The method as claimed in claim 21, wherein the method comprises administering the first immunogenic composition or vaccine to the turkey or chicken at approximately 14 days of age and at 2 to 4 weeks after administering the first immunogenic composition or vaccine, administering the second immunogenic composition or vaccine to the turkey or chicken.

23. The method as claimed in claim 21, wherein the second immunogenic composition or vaccine is an emulsion.

24. A method for preparing an immunogenic composition or vaccine for immunizing or vaccinating a bird against avian *pneumovirus* comprising admixing *pnuemovirus* C990427 a sample of which is deposited with the CNCM under accession number I-2353, with a vehicle or excipient which is veterinarily acceptable, and, optionally, with an adjuvant.

25. The method of claim 24 wherein the bird is a gallinacean.

26. The method as claimed in claim 24, wherein the bird is a duck.

27. An immunogenic composition or vaccine against avian *pneumovirus*, comprising an antigen of avian *pneumovirus* C990427, a sample of which is deposited with the CNCM under the accession number I-2353, in a vehicle or excipient which is veterinarily acceptable and, optionally, an adjuvant.

28. The method as claimed in claim 25, wherein the bird is a duck.

29. The immunogenic composition or vaccine as claimed in claim 4, wherein the aqueous adjuvant is aluminum hydroxide.

30. The immunogenic composition or vaccine as claimed in claim 3, comprising from $10^2$ to $10^4$ CCID50 per dose.

31. The immunogenic composition or vaccine as claimed in claim 6, wherein the avian pathogenic agent is selected from the group consisting of Newcastle disease virus, infectious bronchitis virus, infectious bursal disease virus, duck parvovirus and avian *pneumovirus*.

32. The immunogenic composition or vaccine as claimed in claim 8, wherein the aqueous adjuvant is aluminum hydroxide.

33. The immunogenic composition or vaccine as claimed in claim 8, wherein the emulsion is a water-in-oil emulsion.

34. The immunogenic composition or vaccine as claimed in claim 7, comprising from $10^5$ to $10^7$ CCID50 per dose before inactivation.

35. The immunogenic composition or vaccine as claimed in claim 11, wherein the avian pathogenic agent is selected from the group consisting of Newcastle disease virus, infectious bronchitis virus, infectious bursal disease virus, egg drop syndrome adenovirus, duck parovirus, *paramyxovirus* type III and avian *pneumovirus*.

36. The method as claimed in claim 12, wherein the bird is a duck.

37. The method as claimed in claim 12, wherein the bird is a gallinacean.

38. The method as claimed in claim 12, wherein the bird is a hen.

39. The method as claimed in claim 12, wherein the bird is a turkey.

40. The method as claimed in claim 12, wherein the bird is a chicken.

41. The method as claimed in claim 14, wherein the aqueous adjuvant is aluminum hydroxide.

42. The method as claimed in claim 16 wherein the immunogenic composition or vaccine in the administering step is attenuated and the immunogenic composition or vaccine in the further administering is adjuvented and inactivated.

43. The method as claimed in claim 18, wherein the aqueous adjuvant is aluminum hydroxide.

44. The method as claimed in claim 13, wherein the immunogenic composition or vaccine in the administering step is unattenuated.

45. The method as claimed in claim 14, wherein the immunogenic composition or vaccine in the administering step is attenuated.

46. The method as claimed in claim 12, wherein the administering is in ovo.

47. The method as claimed in claim 46, wherein the in ovo administering is between 4 and 1 day(s) before hatching.

48. The method as claimed in claim 47, wherein the in ovo administering is 3 days before hatching.

* * * * *

UNITED STATES PATENT AND TRADEMARK OFFICE
CERTIFICATE OF CORRECTION

PATENT NO. : 6,919,084 B2  Page 1 of 1
DATED : July 19, 2005
INVENTOR(S) : Sylvan Gabriel Goutebroze It is certified that error appears in the above-identified patent and that said Letters Patent is hereby corrected as shown below:

Column 10,
Line 47, please replace "admimistering" with -- administering --.

Signed and Sealed this

Thirteenth Day of September, 2005

JON W. DUDAS
*Director of the United States Patent and Trademark Office*